(12) United States Patent
Conrado et al.

(10) Patent No.: US 11,053,517 B2
(45) Date of Patent: Jul. 6, 2021

(54) INTERMITTENT ELECTROLYSIS STREAMS

(71) Applicant: LanzaTech, Inc., Skokie, IL (US)

(72) Inventors: Robert John Conrado, Skokie, IL (US); Sean Dennis Simpson, Skokie, IL (US); Christophe Daniel Mihalcea, Skokie, IL (US)

(73) Assignee: LanzaTech, Inc., Skokie, IL (US)

( * ) Notice: Subject to any disclaimer, the term of this patent is extended or adjusted under 35 U.S.C. 154(b) by 95 days.

(21) Appl. No.: 16/373,071

(22) Filed: Apr. 2, 2019

(65) Prior Publication Data
US 2019/0323042 A1 Oct. 24, 2019

Related U.S. Application Data

(60) Provisional application No. 62/660,298, filed on Apr. 20, 2018.

(51) Int. Cl.
*C12P 7/26* (2006.01)
*C12P 5/02* (2006.01)
(Continued)

(52) U.S. Cl.
CPC .............. *C12P 7/26* (2013.01); *C12M 21/12* (2013.01); *C12P 5/026* (2013.01); *C12P 7/04* (2013.01); *C25B 1/02* (2013.01); *C25B 15/08* (2013.01)

(58) Field of Classification Search
CPC .... C12P 7/065; C12P 7/54; C12P 7/16; C12P 7/18; C12P 7/00; C12P 7/06; C12P 7/08; C12P 1/04; C12P 5/00; C12P 5/02; C12P 5/026; C12P 7/04; C12P 7/14; C12P 7/26; C12P 7/625; C12P 1/00; C12P 5/023; C12P 7/52; C12P 7/40; C12P 7/6463; C12P 21/02; C12P 7/64; C12P 13/04; C12P 21/00; C12P 7/10; C12P 39/00; C12P 3/00; C12P 7/649; Y02E 50/10; Y02E 50/30; Y02E 60/366; Y02E 50/16; Y02E 20/16; Y02E 20/18; Y02E 50/13; Y02E 60/527; Y02E 60/36; Y02E 50/17; Y02E 50/343; Y02E 60/50; Y02E 60/528; C12M 43/00; C12M 21/04; C12M 21/12; C12M 29/06; C12M 43/04; C12M 45/07; C12M 29/18; C12M 29/24; C12M 41/32; C12M 41/34; C12M 43/02; C12M 23/34; C12M 29/02; C12M 29/08; C12M 29/20; C12M 47/02; C12M 43/08; C12M 1/00; C12M 43/06; C12M 23/58; C01B 2203/0233; C01B 2203/0283; C01B 2203/043; C01B 2203/061; C01B 3/38; C01B 2203/06; C01B 2203/1058; C01B 2203/0244; C01B 2203/025; C01B 2203/0405; C01B 2203/0475; C01B 2203/062; C01B 2203/0872; C01B 2203/1241; C01B 2203/148; C01B 32/50; C01B 3/48; C01B 3/50; C01B 13/02; C01B 17/02; C01B 17/027; C01B 17/48; C01B 17/74; C01B 2203/0205; C01B 2203/0445; C01B 32/05; C01B 32/21; C01B 3/32; Y02P 20/133; Y02P 20/151; Y02P 20/152; Y02P 20/59; Y02P 10/143; Y02P 30/40; Y02P 30/446; Y02P 20/00; Y02P 20/129; Y02P 20/132; Y02P 20/146; Y02P 30/20; Y02P 20/10; Y02P 20/142; Y02P 20/145; Y02P 20/582; Y02P 30/00; C10G 2300/708; C10G 9/36; C10G 2400/02; C10G 2/50; C10G 11/18; C10G 2300/1011; C10G 1/00; C10G 1/02; C10G 1/10; C10G 31/08; C10G 33/00; C10G 45/00; C10G 57/00; C10G 75/04; C10G 7/00; C10G 7/003; C10G 7/06; C10J 2300/0943; C10J 2300/1681; C10J 2300/1846; C10J 2300/093; C10J 2300/0946; C10J 3/72; C10K 3/026;

(Continued)

(56) References Cited

U.S. PATENT DOCUMENTS 9,085,785 B2  7/2015  Reed et al.
9,157,058 B2  10/2015  Dalla-Betta et al.
(Continued)

FOREIGN PATENT DOCUMENTS

WO  2012/058508 A3  3/2012
WO  2012058508  *  5/2012

OTHER PUBLICATIONS

International Search Report for International Patent Application PCT/US2019/0025373, Korean Intellectual Property Office, dated Jul. 15, 2019.

*Primary Examiner* — Deborah K Ware
(74) *Attorney, Agent, or Firm* — Frank S. Molinaro

(57) ABSTRACT

The invention provides for methods by which the economics of the gas fermentation process are improved. The invention provides for the integration of a fermentation process, with an industrial process and an electrolyzer process. The invention provides for the intermittent supply of electrolyzer feedstock from the electrolyzer process to the bioreactor for fermentation. The electrolyzer feedstock may displace at least a portion of the C1 feedstock from the industrial process. The electrolyzer feedstock may supplement the C1 feedstock from the industrial process. Whether or not the electrolyzer feedstock supplements or displaces the C1 feedstock with electrolyzer feedstock may be based upon a function of the cost per unit of the C1 feedstock, the cost per unit of the electrolyzer feedstock, and the value per unit of the fermentation product.

17 Claims, 8 Drawing Sheets

(51) Int. Cl.
*C25B 15/08* (2006.01)
*C12M 1/00* (2006.01)
*C25B 1/02* (2006.01)
*C12P 7/04* (2006.01)
*C12N 1/20* (2006.01)

(58) Field of Classification Search
CPC .... C10L 1/023; C10L 1/04; C10L 1/06; C10L 2290/10; C10L 2290/26; C10L 2290/42; C10L 2290/542; C10L 2290/546; C10L 1/02; C10L 2290/543; C10L 2290/545; C10L 3/00; C10L 3/08; C10L 3/10; C10L 2290/544; C10L 9/10; C25B 15/08; C25B 1/02; C25B 1/04; C25B 1/00; C25B 1/003; C25B 3/04; C25B 15/02; C07C 29/1518; C07C 31/04; C07C 31/08; A23K 10/12; A23K 10/16; B01D 2251/206; B01D 2251/304; B01D 2251/306; B01D 2251/604; B01D 2251/606; B01D 2252/103; B01D 2252/2021; B01D 2252/2026; B01D 2252/204; B01D 2257/304; B01D 2257/504; B01D 2258/0283; B01D 2258/05; B01D 2259/124; B01D 53/1406; B01D 53/1425; B01D 53/1462; B01D 53/1475; B01D 53/1493; B01D 53/18; B01D 53/62; B01D 53/75; B01D 53/78; B01D 2257/50; B01D 2257/502; B01D 3/06; B01D 53/48; C12F 3/10; C12N 1/20; C12N 1/30; C12N 15/52; C12N 15/70; C12N 9/0006; C12N 9/0051; C12N 1/12; C12N 15/74; C12N 1/36; C12N 13/00; C12N 15/01; C12N 1/005; C12N 1/06; C12R 1/02; C12R 1/145; C12R 1/01; H01M 8/06; H01M 8/184; H01M 10/54; H01M 8/00; H01M 8/16; Y10S 204/04; C12Y 101/05006; C12Y 108/05004; Y02C 20/40; Y02C 10/12; Y02W 10/33; Y02W 10/37; Y02W 30/40; Y02W 10/30; Y02W 30/84; A23J 1/008; A23J 3/20; A23L 11/45; A23L 33/135; C02F 1/008; C02F 1/20; C02F 1/66; C02F 2101/10; C02F 2101/32; C02F 2103/007; C02F 2301/046; C02F 2303/10; C02F 3/322; C02F 9/00; C02F 1/00; C05D 7/00; F01K 25/103; F01K 7/16; F25J 2205/20; F25J 2210/66; F25J 2215/04; F25J 2260/30; F25J 2260/44; F25J 2260/80; F25J 3/0209; F25J 3/0233; F25J 3/0266; F25J 3/04533; F25J 3/04563; A61P 35/00; B01J 19/0093; B01J 19/24; B01J 2219/00864; B01J 2219/00867; B01J 2219/00871; B01J 2231/625; B01J 2/00; B01J 6/008; B02C 23/00; B03C 1/00; B09B 5/00; B22F 2009/001; B22F 3/10; B22F 9/00; B22F 17/00; C01G 21/02; C22B 13/00; C22B 15/00; C22B 21/00; C22B 7/00; C22B 9/00; F27B 17/00; H02K 55/02; H02K 7/09

See application file for complete search history.

(56) References Cited

U.S. PATENT DOCUMENTS

| | | | |
|---|---|---|---|
| 10,358,662 B2 * | 7/2019 | Simpson | C12P 7/54 |
| 2010/0120104 A1 | 5/2010 | Reed | |
| 2012/0003705 A1 | 1/2012 | Jin et al. | |
| 2013/0078690 A1 | 3/2013 | Reed | |
| 2013/0189763 A1 | 7/2013 | Dalla-Betta et al. | |
| 2016/0102287 A1 | 4/2016 | Dalla-Betta et al. | |
| 2017/0218404 A1 | 8/2017 | Simpson et al. | |
| 2019/0249315 A1 * | 8/2019 | Mihalcea | C25B 15/08 |

* cited by examiner

INTERMITTENT ELECTROLYSIS STREAMS

CROSS-REFERENCE TO A RELATED APPLICATION

The application claims the benefit of U.S. Provisional Application No. 62/660,298 filed Apr. 20, 2018, the contents of which are hereby incorporated by reference.

FIELD OF THE INVENTION

The invention relates to processes and methods for improving the economics of a gas fermentation process. In particular, the invention relates to the combination of a fermentation process with an industrial process and an electrolyzer process where the electrolyzer feedstock from the electrolyzer process is intermittently passed to a bioreactor for fermentation.

BACKGROUND OF THE INVENTION

Carbon dioxide ($CO_2$) accounts for about 76% of global greenhouse gas emissions from human activities, with methane (16%), nitrous oxide (6%), and fluorinated gases (2%) accounting for the balance (United States Environmental Protection Agency). Reduction of greenhouse gas emissions, particularly $CO_2$, is critical to halt the progression of global warming and the accompanying shifts in climate and weather.

It has long been recognized that catalytic processes, such as the Fischer-Tropsch process, may be used to convert gases containing carbon dioxide ($CO_2$), carbon monoxide (CO), and/or hydrogen ($H_2$), into a variety of fuels and chemicals. Recently, however, gas fermentation has emerged as an alternative platform for the biological fixation of such gases. In particular, C1-fixing microorganisms have been demonstrated to convert gases containing $CO_2$, CO, $CH_4$, and/or $H_2$ into products such as ethanol and 2,3-butanediol.

Such gasses may be derived, for example, from industrial processes, including gas from carbohydrate fermentation, gas from cement making, pulp and paper making, steel making, oil refining and associated processes, petrochemical production, coke production, anaerobic or aerobic digestion, synthesis gas (derived from sources including but not limited to biomass, liquid waste streams, solid waste streams, municipal streams, fossil resources including natural gas, coal and oil), natural gas extraction, oil extraction, metallurgical processes, for production and/or refinement of aluminium, copper, and/or ferroalloys, geological reservoirs, and catalytic processes (derived from steam sources including but not limited to steam methane reforming, steam naphtha reforming, petroleum coke gasification, catalyst regeneration—fluid catalyst cracking, catalyst regeneration-naphtha reforming, and dry methane reforming).

With particular industrial processes the supply of gas may be insufficient for the fermentation process. When the supply of gas becomes insufficient for the fermentation process, the production rate of the fermentation process is less than optimal resulting in less products produced than what the fermentation process would otherwise be capable of producing.

Additionally, with a constantly adjusting market, the value of the products produced by the gas fermentation process varies. When the value of the products produced by the gas fermentation are high in comparison with the cost of producing such products, it is advantageous to increase the production rate of the fermentation process.

By increasing the production rate of the fermentation process at times when the market value of such products is high relative to the cost of producing such products, the economics of the fermentation process may be optimized.

Accordingly, there remains a need for improved integration of fermentation processes with industrial processes, where the problems associated with the supply of feedstock are curtailed and the fermentation process is capable of producing at maximum levels at times when such production is economically optimal.

BRIEF SUMMARY OF THE INVENTION

The invention provides a method for improving the performance and/or the economics of a fermentation process, the fermentation process defining a bioreactor containing a bacterial culture in a liquid nutrient medium, wherein the method comprises passing a C1 feedstock comprising one or both of CO and $CO_2$ from an industrial process to the bioreactor, wherein the C1 feedstock has a cost per unit, intermittently passing an electrolyzer feedstock comprising one or both of CO and $H_2$ from an electrolyzer process to the bioreactor, wherein the electrolyzer feedstock has a cost per unit, and fermenting the culture to produce one or more fermentation products, wherein each of the one or more fermentation products has a value per unit. In certain instances, multiple electrolyzer processes are utilized in order to provide one or both of CO and $H_2$ to the bioreactor.

In certain instances, the C1 feedstock is derived from an industrial process selected from the group comprising: gas from carbohydrate fermentation, gas from cement making, pulp and paper making, steel making, oil refining and associated processes, petrochemical production, coke production, anaerobic or aerobic digestion, synthesis gas (derived from sources including but not limited to biomass, liquid waste streams, solid waste streams, municipal streams, fossil resources including natural gas, coal and oil), natural gas extraction, oil extraction, metallurgical processes, for production and/or refinement of aluminium, copper, and/or ferroalloys, geological reservoirs, and catalytic processes (derived from steam sources including but not limited to steam methane reforming, steam naphtha reforming, petroleum coke gasification, catalyst regeneration—fluid catalyst cracking, catalyst regeneration-naphtha reforming, and dry methane reforming). In certain instances, the C1 feedstock is derived from a combination of two or more sources. In certain instances, the C1 feedstock may further comprise $H_2$.

In certain instances, the electrolyzer feedstock comprises CO. The electrolyzer feedstock comprising CO is derived from the electrolysis of a $CO_2$-containing gaseous substrate. The $CO_2$-containing gaseous substrate may be derived from any gas stream containing $CO_2$. In particular instances, this $CO_2$-containing gas stream is derived at least in part from the group comprising: gas from carbohydrate fermentation, gas from cement making, pulp and paper making, steel making, oil refining and associated processes, petrochemical production, coke production, anaerobic or aerobic digestion, synthesis gas (derived from sources including but not limited to biomass, liquid waste streams, solid waste streams, municipal streams, fossil resources including natural gas, coal and oil), natural gas extraction, oil extraction, metallurgical processes, for production and/or refinement of aluminium, copper, and/or ferroalloys, geological reservoirs, and catalytic processes (derived from steam sources including but not limited to steam methane reforming, steam naphtha reforming, petroleum coke gasification, catalyst regeneration—fluid catalyst cracking, catalyst regeneration-naphtha reforming, and dry methane reforming). In particular instances, the $CO_2$-containing gaseous substrate is derived from a combination of two or more sources.

In certain instances, the electrolyzer feedstock comprises $H_2$. The electrolyzer feedstock comprising $H_2$ is derived from the electrolysis of water ($H_2O$). This water may be obtained from numerous sources. In various instances, the water may be obtained from the industrial process and/or the fermentation process. In various instances, the water may be obtained from a waste water treatment process. In particular instances, the water is obtained from a combination of two or more sources.

In particular instances, the invention improves the economics of the fermentation process by displacing at least a portion of the C1 feedstock from the industrial process with electrolyzer feedstock from the electrolyzer process. In various instances when the electrolyzer feedstock comprises $H_2$, the electrolyzer feedstock displaces at least a portion of the C1 feedstock from the industrial process as a means to adjust the molar ratio of $H_2:CO:CO_2$ of the feedstock being passed to the fermentation process. In certain instances, the electrolyzer feedstock comprising $H_2$ increases the molar ratio of $H_2$ in the feedstock being passed to the fermentation process.

The displacement of the C1 feedstock from the industrial process with electrolyzer feedstock from an electrolyzer process may be completed, at least in part, as a function of the cost per unit of the C1 feedstock and the cost per unit of the electrolyzer feedstock. In certain instances, the electrolyzer feedstock displaces at least a portion of the C1 feedstock when the cost per unit of electrolyzer feedstock is less than the cost per unit of C1 feedstock.

In particular instances, the invention improves the economics of the fermentation process by supplementing at least a portion of the C1 feedstock from the industrial process with electrolyzer feedstock from the electrolyzer process. The supplementing of the C1 feedstock with the electrolyzer feedstock may be completed, at least in part, when the supply of the C1 feedstock is insufficient for the fermentation process.

In certain instances, the electrolyzer feedstock supplements at least a portion of the C1 feedstock as a function of the cost per unit of the electrolyzer feedstock and the value per unit of the fermentation product.

In certain instances, the electrolyzer feedstock supplements at least a portion of the C1 feedstock as a function of the cost per unit of the C1 feedstock, the cost per unit of the electrolyzer feedstock, and the value per unit of the fermentation product.

In certain instances, the electrolyzer feedstock supplements the C1 feedstock when the cost per unit of the electrolyzer feedstock is less than the value per unit of the fermentation product. The cost per unit of electrolyzer feedstock may be less than the value per unit of the fermentation product when the cost of electricity is reduced. In certain instances, the cost of electricity is reduced due to the electricity being sourced from a renewable energy source. In certain instances, the renewable energy source is selected from the group consisting of solar, hydro, wind, geothermal, biomass, and nuclear.

The supplementing of the C1 feedstock comprising $CO_2$ with electrolyzer feedstock comprising $H_2$ may result in a number of benefits, including but not limited to, increasing the amount of $CO_2$ fixed in the one or more fermentation products. Therefore, in various instances, electrolyzer feedstock comprising $H_2$ supplements the C1 feedstock comprising $CO_2$ so as to increase the amount of $CO_2$ fixed in the one or more fermentation products.

In particular instances, the C1 feedstock contains proportions of various constituents that necessitate removal. In these instances, the C1 feedstock is treated to remove one or more constituent prior to passing the C1 feedstock to the bioreactor. The constituents removed from the C1 feedstock may be selected from the group comprising: sulphur compounds, aromatic compounds, alkynes, alkenes, alkanes, olefins, nitrogen compounds, phosphorous-containing compounds, particulate matter, solids, oxygen, oxygenates, halogenated compounds, silicon containing compounds, carbonyls, metals, alcohols, esters, ketones, peroxides, aldehydes, ethers, and tars.

In particular instances, the electrolyzer feedstock contains proportions of various constituents that necessitate removal. In these instances, the electrolyzer feedstock is treated to remove one or more constituent prior to passing the electrolyzer feedstock to the bioreactor. The constituents removed from the electrolyzer feedstock may be selected from the group comprising: sulphur compounds, aromatic compounds, alkynes, alkenes, alkanes, olefins, nitrogen compounds, phosphorous-containing compounds, particulate matter, solids, oxygen, oxygenates, halogenated compounds, silicon containing compounds, carbonyls, metals, alcohols, esters, ketones, peroxides, aldehydes, ethers, and tars. In particular instances at least one constituent removed from the electrolyzer feedstock comprises oxygen. At least one of the constituents removed may be produced, introduced, and/or concentrated by the electrolyzer process. For example, oxygen may be produced, introduced, and/or concentrated by the electrolysis of carbon dioxide. In various instances, oxygen is a by-product of the electrolyzer process. In particular embodiments, oxygen is produced and/or concentrated in the electrolyzer process.

Oxygen is a microbe inhibitor for many bacterial cultures. As such, oxygen may be inhibiting to the downstream fermentation process. In order to pass a non-inhibiting gas stream to the bioreactor where it may be fermented, at least a portion of oxygen, or other constituent, may need to be removed from the electrolyzer feedstock by one or more removal module.

In certain instances, the C1 feedstock is passed to the fermentation process at pressure. In these instances, the C1 feedstock from the industrial process is passed to one or more pressure module prior to being passed to the bioreactor for fermentation.

In certain instances, the electrolyzer feedstock is passed to the fermentation process at pressure. In these instances, the electrolyzer feedstock from the electrolyzer process is passed to one or more pressure module prior to being passed to the bioreactor for fermentation.

Additionally, the electrolyzer process may be completed at pressure. When completed at pressure, the material being electrolyzed is pressurized prior to being fed to the electrolyzer process. In certain instances, the material being electrolyzed is a $CO_2$-containing gas stream. In instances where the $CO_2$-containing gas stream is pressurized prior to being electrolyzed, the $CO_2$-containing gas stream may be passed to a pressure module prior to being passed to the electrolysis module.

In at least one embodiment, the method reduces the associated costs of producing various fermentation products. At least one of the one or more of the fermentation products may be selected from the group consisting of ethanol, acetate, butyrate, 2,3-butanediol, lactate, butene, butadiene, ketones, methyl ethyl ketone, ethylene, acetone, isopropanol, lipids, 3-hydroypropionate, isoprene, fatty acids, 2-butanol, 1,2-propanediol, 1-propanol, and C6-C12 alcohols. At least one of the fermentation products may be further converted to at least one component of diesel, jet fuel, and/or gasoline.

At least one of the one or more fermentation products may be biomass produced by the culture. At least a portion of the microbial biomass may be converted to a single cell protein (SCP). At least a portion of the single cell protein may be utilized as a component of animal feed.

In at least one embodiment, the electrolyzer process is powered, at least in part, by a renewable energy source. In certain instances, the renewable energy source is selected from the group consisting of solar, hydro, wind, geothermal, biomass, and nuclear.

In certain embodiments, the industrial process may further produce a post-fermentation gaseous substrate. In various instances, this post-fermentation gaseous substrate comprises at least a portion of $CO_2$. In particular embodiments the post-fermentation gaseous substrate is passed to the electrolyzer process.

In particular instances, the post-fermentation gaseous substrate contains proportions of various constituents that necessitate removal. In these instances, the post-fermentation gaseous substrate is treated to remove one or more constituent prior to passing the post-fermentation gaseous substrate to the electrolyzer process. The constituents removed from the post-fermentation gaseous substrate may be selected from the group comprising: sulphur compounds, aromatic compounds, alkynes, alkenes, alkanes, olefins, nitrogen compounds, phosphorous-containing compounds, particulate matter, solids, oxygen, oxygenates, halogenated compounds, silicon containing compounds, carbonyls, metals, alcohols, esters, ketones, peroxides, aldehydes, ethers, and tars.

In particular instances at least one constituent removed from the post-fermentation gaseous substrate comprises sulphur. At least one of these constituents removed may be produced, introduced, and/or concentrated by the fermentation process. For example, sulphur, in the form of hydrogen sulfide ($H_2S$) may be produced, introduced, and/or concentrated by the fermentation process. In particular embodiments, hydrogen sulfide is introduced in the fermentation process. In various embodiments, the post-fermentation gaseous substrate comprises at least a portion of hydrogen sulfide. Hydrogen sulfide may be a catalyst inhibitor. As such, the hydrogen sulfide may be inhibiting to particular electrolysers. In order to pass a non-inhibiting post-fermentation gaseous substrate to the electrolyser at least a portion of the hydrogen sulfide, or other constituent present in the post-fermentation gaseous substrate, may need to be removed by one or more removal module.

In various embodiments, the constituent removed from the post-fermentation gaseous substrate, the industrial feedstock, and/or the electrolyzer feedstock is a microbe inhibitor and/or a catalyst inhibitor.

At least one removal module may be selected from the group comprising: hydrolysis module, acid gas removal module, deoxygenation module, catalytic hydrogenation module, particulate removal module, chloride removal module, tar removal module, and hydrogen cyanide removal module.

In certain instances, the electrolyzer process may produce a carbon monoxide enriched stream and an oxygen enriched stream. In various instances, at least a portion of the separated carbon monoxide enriched stream may be passed to the bioreactor for fermentation. In some instances, the oxygen enriched stream may be passed to the industrial process to further improve the performance and/or economics of the industrial process.

In various embodiments where the electrolyzer feedstock comprises $H_2$, the $H_2$ may improve the fermentation substrate composition. Hydrogen provides energy required by the microorganism to convert carbon containing gases into useful products. When optimal concentrations of hydrogen are provided, the microbial culture can produce the desired fermentation products, for example ethanol, without the co-production of carbon dioxide.

Preferably, the bacterial culture in the bioreactor comprises a carboxydotrophic bacterium. The carboxydotrophic bacterium may be selected from the group comprising *Moorella, Clostridium, Ruminococcus, Acetobacterium, Eubacterium, Butyribacterium, Oxobacter, Methanosarcina*, and *Desulfotomaculum*. Preferably, the carboxydotrophic bacterium is *Clostridium autoethanogenum*.

In one or more embodiment, the invention (i) decreases the cost associated with producing one or more fermentation product and/or (ii) increases the total amount of carbon converted to product, compared to a process without an electrolyzer process.

DETAILED DESCRIPTION OF THE INVENTION

Figure 1:
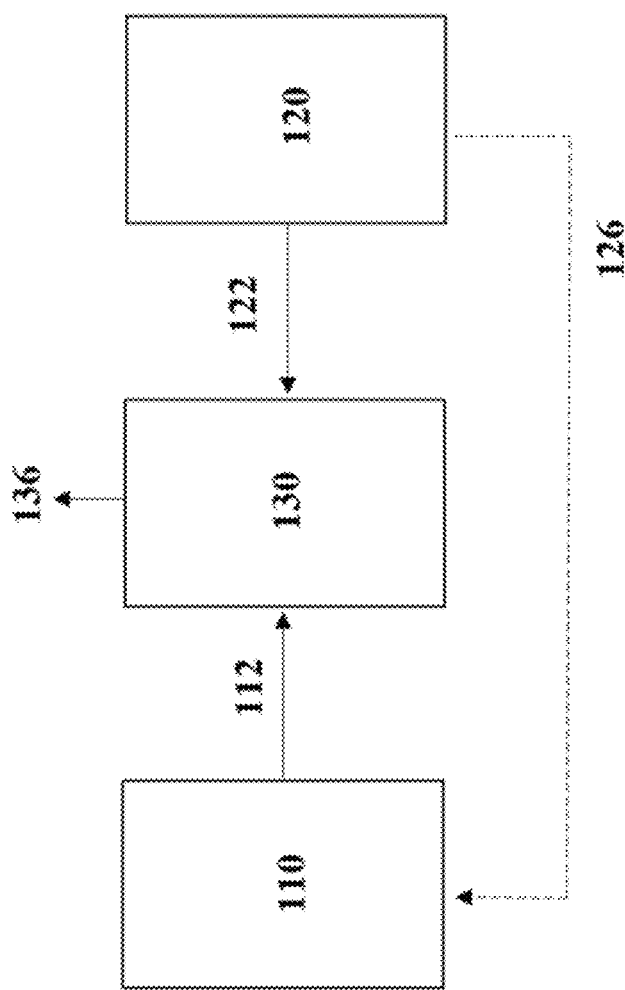
FIG. 1 is a schematic flow diagram depicting the integration of an industrial process and an electrolyzer process with a fermentation process.

The inventors have identified that the integration of a gas fermentation process with an industrial process and an electrolyzer process, where the electrolyzer process intermittently supplies an electrolyzer feedstock, is capable of substantially improving the performance and/or economics of the fermentation process.

Definitions

Unless otherwise defined, the following terms as used throughout this specification are defined as follows:

The term "electrolyzer feedstock", may include any substrate leaving the electrolyzer. In various instances, the electrolyzer feedstock is comprised of CO, $H_2$, or combinations thereof. In certain instances, the electrolyzer feedstock may contain portions of unconverted $CO_2$. Preferably, the electrolyzer feedstock is fed from the electrolyzer process to the fermentation process.

The term "C1 feedstock", may include any substrate leaving the industrial process. In various instances, the C1 feedstock is comprised of CO, $H_2$, $CO_2$, or combinations thereof. Preferably, the C1 feedstock is fed from the industrial process to the fermentation process.

The terms "improving the economics", "optimizing the economics" and the like, when used in relationship to a fermentation process, include, but are not limited to, the increase of the amount of one or more of the products produced by the fermentation process during periods of time in which the value of the products produced is high relative to the cost of producing such products. The economics of the fermentation process may be improved by way of increasing the supply of feedstock to the bioreactor, which may be achieved for instance by supplementing the C1 feedstock from the industrial process with electrolyzer feedstock from the electrolyzer process. The additional supply of feedstock may result in the increased efficiency of the fermentation process. Another means of improving the economics of the fermentation process is to select feedstock based upon the relative cost of the feedstock available. For example, when the cost of the C1 feedstock from the industrial process is higher than the cost of the electrolyzer feedstock from the electrolyzer process, the electrolyzer feedstock may be utilized to displace at least a portion of the C1 feedstock. By selecting feedstock based upon the cost of such feedstock the cost of producing the resulting fermentation product is reduced.

The electrolyzer process is capable of supplying feedstock comprising one or both of $H_2$ and CO. The "cost per unit of electrolyzer feedstock" may be expressed in terms of any given product produced by the fermentation process and any electrolyzer feedstock, for example for the production of ethanol with the electrolyzer feedstock defined as $H_2$, the cost per unit of electrolyzer feedstock is defined by the following equation:

$$\left(\frac{\$z}{MWh}\right) \times \left(\frac{1 MWh}{3.6\ GJ_{electricity}}\right) \times \left(x \frac{GJ_{electricity}}{GJ_{H2}}\right) \times \left(y \frac{GJ_{H2}}{GJ_{ethanol}}\right)$$

where z represents the cost of power, x represents the electrolysis efficiency, and y represents the yield of ethanol.

For the production of ethanol with electrolyzer feedstock defined as CO, the cost per unit of electrolyzer feedstock is defined by the following equation:

$$\left(\frac{\$z}{MWh}\right) \times \left(\frac{1 MWh}{3.6\ GJ_{electricity}}\right) \times \left(x \frac{GJ_{electricity}}{GJ_{CO}}\right) \times \left(y \frac{GJ_{CO}}{GJ_{ethanol}}\right)$$

where z represents the cost of power, x represents the electrolysis efficiency, and y represents the yield of ethanol.

In addition to the cost of feedstock, the fermentation process includes "production costs." The "production costs" exclude the cost of the feedstock. "Production costs", "marginal cost of production", and the like, include the variable operating costs associated with running the fermentation process. This value may be dependent on the product being produced. The marginal cost of production may be represented by a fixed cost per unit of product, which may be represented in terms of the heating value of combustion of the product. For example, the calculation of the marginal cost of production for ethanol is defined by the following equation:

$$\left(\frac{\$c}{metric\ ton}\right) \times \left(\frac{1\ metric\ ton}{26.8\ GJ_{ethanol}}\right)$$

where c represents the variable operating costs associated with running the bioreactor and 26.8 GJ represents the lower heating value of combustion of ethanol. In certain instances, the variable operating costs associated with running the bioreactor, c, is $200 for ethanol excluding the price of $H_2/CO/CO_2$.

The fermentation process is capable of producing a number of products. Each product defining a different value. The "value of the product" may be determined based upon the current market price of the product and the heating value of combustion of the product. For example, the calculation for the value of ethanol is defined by the following equation:

$$\left(\frac{\$z}{metric\ ton}\right) \times \left(\frac{1\ metric\ ton}{26.8\ GJ_{ethanol}}\right)$$

where z is the current value of ethanol per metric ton and 26.8 GJ represents the lower heating value of combustion of ethanol.

To optimize the economics of the fermentation process, the value of the product produced must exceed the "cost of producing" such product. The cost of producing a product is defined as the sum of the "cost of feedstock" and the "marginal cost of production." The economics of the fermentation process may be expressed in terms of a ratio defined by the value of product produced compared to the cost of producing such product. The economics of the fermentation process is improved as the ratio of the value of the product compared to the cost of producing such product increases. The economics of the fermentation process may be dependent on the value of the product produced, which may change dependent, at least in part, on the fermentation process implemented, including but not limited to the bacterial culture and/or the composition of the gas used in the fermentation process. When ethanol is the product produced by the fermentation process the economics may be determined by the following ratio:

$$\left(\frac{\$z}{GJ_{ethanol}}\right) : \left(\frac{\$x}{GJ_{ethanol}}\right) + \left(\frac{\$y}{GJ_{ethanol}}\right)$$

where z represents the value of ethanol, x represents the cost of feedstock, and y represents the marginal cost of production (excluding feedstock).

The terms "increasing the efficiency", "increased efficiency" and the like, when used in relation to a fermentation process, include, but are not limited to, increasing one or more of the rate of growth of microorganisms catalysing the fermentation, the growth and/or product production rate at elevated product concentrations, the volume of desired product produced per volume of substrate consumed, the rate of production or level of production of the desired product, and the relative proportion of the desired product produced compared with other by-products of the fermentation. In certain instances, the electrolyzer feedstock increases the efficiency of the fermentation process.

The term "insufficient" and the like, when used in relation to the supply of feedstock for the fermentation process, includes, but is not limited to, lower than optimal amounts, whereby the fermentation process produces less quantity of fermentation product than the fermentation process otherwise would had the fermentation process been supplied with higher amounts of feedstock. For example, the supply of feedstock may become insufficient at times when the industrial process is not providing enough C1 feedstock to adequately supply the fermentation process. Preferably, the fermentation process is supplied with optimal amounts of feedstock such that the quantity of fermentation product is not limited by the feedstock supply.

"C1-containing gaseous substrate" may include any gas which contains one or both of carbon dioxide and carbon monoxide. The gaseous substrate will typically contain a significant proportion of $CO_2$, preferably at least about 5% to about 100% $CO_2$ by volume. Additionally, the gaseous substrate may contain one or more of hydrogen ($H_2$), oxygen ($O_2$), nitrogen ($N_2$), and/or methane ($CH_4$).

While it is not necessary for the substrate to contain any hydrogen, the presence of $H_2$ should not be detrimental to product formation in accordance with methods of the invention. In particular embodiments, the presence of hydrogen results in an improved overall efficiency of alcohol production. In one embodiment, the substrate comprises about 30% or less $H_2$ by volume, 20% or less $H_2$ by volume, about 15% or less $H_2$ by volume or about 10% or less $H_2$ by volume. In other embodiments, the substrate stream comprises low concentrations of $H_2$, for example, less than 5%, or less than 4%, or less than 3%, or less than 2%, or less than 1%, or is substantially hydrogen free.

The substrate may also contain some CO for example, such as about 1% to about 80% CO by volume, or 1% to about 30% CO by volume. In one embodiment, the substrate comprises less than or equal to about 20% CO by volume. In particular embodiments, the substrate comprises less than or equal to about 15% CO by volume, less than or equal to about 10% CO by volume, less than or equal to about 5% CO by volume or substantially no CO.

Substrate composition can be improved to provide a desired or optimum $H_2:CO:CO_2$ molar ratio. The desired $H_2:CO:CO_2$ molar ratio is dependent on the desired fermentation product of the fermentation process. For ethanol, the optimum $H_2:CO:CO_2$ molar ratio would be:

$$(x):(y):\left(\frac{x-2y}{3}\right),$$

where x>2y, in order to satisfy the molar stoichiometry for ethanol production $$(x)H_2 + (y)CO + \left(\frac{x-2y}{3}\right)CO_2 \rightarrow \left(\frac{x+y}{6}\right)C_2H_5OH + \left(\frac{x-y}{2}\right)H_2O.$$

Operating the fermentation process in the presence of hydrogen, has the added benefit of reducing the amount of $CO_2$ produced by the fermentation process. For example, a gaseous substrate comprising minimal $H_2$, will typically produce ethanol and $CO_2$ by the following molar stoichiometry [6 CO+3$H_2$O→$C_2H_5OH$+4 $CO_2$]. As the amount of hydrogen utilized by the C1 fixing bacterium increases, the amount of $CO_2$ produced decreases [i.e., 2 CO+4$H_2$→$C_2H_5OH$+$H_2O$].

When CO is the sole carbon and energy source for ethanol production, a portion of the carbon is lost to $CO_2$ as follows:

6CO+3$H_2$O→$C_2H_5OH$+4$CO_2$($\Delta G°$=−224.90 kJ/mol ethanol)

As the amount of $H_2$ available in the substrate increases, the amount of $CO_2$ produced decreases. At a molar stoichiometric ratio of 1:2 (CO/$H_2$), $CO_2$ production is completely avoided.

5CO+1$H_2$+2$H_2$O→1$C_2H_5OH$+3$CO_2$($\Delta G°$=−204.80 kJ/mol ethanol)

4CO+2$H_2$+1$H_2$O→1$C_2H_5OH$+2$CO_2$($\Delta G°$=−184.70 kJ/mol ethanol)

3CO+3$H_2$→1$C_2H_5OH$+1$CO_2$($\Delta G°$=−164.60 kJ/mol ethanol)

"Gas stream" refers to any stream of substrate which is capable of being passed, for example, from one module to another, from one module to a bioreactor, from one process to another process, and/or from one module to a carbon capture means.

"Reactants" as used herein refer to a substance that takes part in and undergoes change during a chemical reaction. In particular embodiments, the reactants include, but are not limited to, CO and/or $H_2$.

"Microbe inhibitors" as used herein refer to one or more constituent that slows down or prevents a particular chemical reaction or other process including the microbe. In particular embodiments, the microbe inhibitors include, but are not limited to, Oxygen ($O_2$), hydrogen cyanide (HCN), acetylene ($C_2H_2$), and BTEX (benzene, toluene, ethyl benzene, xylene).

"Catalyst inhibitor", "adsorbent inhibitor", and the like, as used herein, refer to one or more substance that decreases the rate of, or prevents, a chemical reaction. In particular embodiments, the catalyst and/or adsorbent inhibitors may include, but are not limited to, hydrogen sulfide ($H_2S$) and carbonyl sulfide (COS).

"Removal module", "clean-up module", "processing module" and the like includes technologies that are capable of either converting and/or removing microbe inhibitors, and/or catalyst inhibitors from the gas stream.

The term "constituents", "contaminants", and the like, as used herein, refers to the microbe inhibitors, and/or catalyst inhibitors that may be found in the gas stream. In particular embodiments, the constituents include, but are not limited to, sulphur compounds, aromatic compounds, alkynes, alkenes, alkanes, olefins, nitrogen compounds, phosphorous-containing compounds, particulate matter, solids, oxygen, oxygenates, halogenated compounds, silicon containing compounds, carbonyls, metals, alcohols, esters, ketones, peroxides, aldehydes, ethers, and tars. Preferably, the constituents removed by the removal module does not include carbon dioxide ($CO_2$).

The term "treated gas" refers to the gas stream that has been passed through at least one removal module and has had one or more constituent removed and/or converted.

The term "carbon capture" as used herein refers to the sequestration of carbon compounds including $CO_2$ and/or CO from a stream comprising $CO_2$ and/or CO and either:

converting the $CO_2$ and/or CO into products; or
converting the $CO_2$ and/or CO into substances suitable for long term storage; or
trapping the $CO_2$ and/or CO in substances suitable for long term storage;
or a combination of these processes.

The term "bioreactor" includes a fermentation device consisting of one or more vessels and/or towers or piping arrangements, which includes the Continuous Stirred Tank Reactor (CSTR), Immobilized Cell Reactor (ICR), Trickle Bed Reactor (TBR), Bubble Column, Gas Lift Fermenter, Static Mixer, a circulated loop reactor, a membrane reactor, such as a Hollow Fibre Membrane Bioreactor (HFM BR) or other vessel or other device suitable for gas-liquid contact. The reactor is preferably adapted to receive a gaseous substrate comprising CO or $CO_2$ or $H_2$ or mixtures thereof. The reactor may comprise multiple reactors (stages), either in parallel or in series. For example, the reactor may comprise a first growth reactor in which the bacteria are cultured and a second fermentation reactor, to which fermentation broth from the growth reactor may be fed and in which most of the fermentation products may be produced.

"Nutrient media" or "Nutrient medium" is used to describe bacterial growth media. Generally, this term refers to a media containing nutrients and other components appropriate for the growth of a microbial culture. The term "nutrient" includes any substance that may be utilised in a metabolic pathway of a microorganism. Exemplary nutrients include potassium, B vitamins, trace metals and amino acids.

The term "fermentation broth" or "broth" is intended to encompass the mixture of components including nutrient media and a culture or one or more microorganisms. It should be noted that the term microorganism and the term bacteria are used interchangeably throughout the document.

The term "acid" as used herein includes both carboxylic acids and the associated carboxylate anion, such as the mixture of free acetic acid and acetate present in a fermentation broth as described herein. The ratio of molecular acid to carboxylate in the fermentation broth is dependent upon the pH of the system. In addition, the term "acetate" includes both acetate salt alone and a mixture of molecular or free acetic acid and acetate salt, such as the mixture of acetate salt and free acetic acid present in a fermentation broth as described herein.

The term "desired composition" is used to refer to the desired level and types of components in a substance, such as, for example, of a gas stream. More particularly, a gas is considered to have a "desired composition" if it contains a particular component (i.e. CO, $H_2$, and/or $CO_2$) and/or contains a particular component at a particular proportion and/or does not contain a particular component (i.e. a constituent harmful to the microorganisms) and/or does not contain a particular component at a particular proportion. More than one component may be considered when determining whether a gas stream has a desired composition.

Unless the context requires otherwise, the phrases "fermenting", "fermentation process" or "fermentation reaction" and the like, as used herein, are intended to encompass both the growth phase and product biosynthesis phase of the gaseous substrate.

A "microorganism" is a microscopic organism, especially a bacterium, archea, virus, or fungus. The microorganism of the invention is typically a bacterium. As used herein, recitation of "microorganism" should be taken to encompass "bacterium."

A "parental microorganism" is a microorganism used to generate a microorganism of the invention. The parental microorganism may be a naturally-occurring microorganism (i.e., a wild-type microorganism) or a microorganism that has been previously modified (i.e., a mutant or recombinant microorganism). The microorganism of the invention may be modified to express or overexpress one or more enzymes that were not expressed or overexpressed in the parental microorganism. Similarly, the microorganism of the invention may be modified to contain one or more genes that were not contained by the parental microorganism. The microorganism of the invention may also be modified to not express or to express lower amounts of one or more enzymes that were expressed in the parental microorganism. In one embodiment, the parental microorganism is *Clostridium autoethanogenum*, *Clostridium ljungdahlii*, or *Clostridium* ragsdalei. In a preferred embodiment, the parental microorganism is *Clostridium autoethanogenum* LZ1561, which was deposited on Jun. 7, 2010 with Deutsche Sammlung von Mikroorganismen and Zellkulturen GmbH (DSMZ) located at Inhoffenstraß 7B, D-38124 Braunschweig, Germany on Jun. 7, 2010 under the terms of the Budapest Treaty and accorded accession number DSM23693. This strain is described in International Patent Application No. PCT/NZ2011/000144, which published as WO 2012/015317.

The term "derived from" indicates that a nucleic acid, protein, or microorganism is modified or adapted from a different (i.e., a parental or wild-type) nucleic acid, protein, or microorganism, so as to produce a new nucleic acid, protein, or microorganism. Such modifications or adaptations typically include insertion, deletion, mutation, or substitution of nucleic acids or genes. Generally, the microorganism of the invention is derived from a parental microorganism. In one embodiment, the microorganism of the invention is derived from *Clostridium autoethanogenum*, *Clostridium ljungdahlii*, or *Clostridium* ragsdalei. In a preferred embodiment, the microorganism of the invention is derived from *Clostridium autoethanogenum* LZ1561, which is deposited under DSMZ accession number DSM23693.

"Wood-Ljungdahl" refers to the Wood-Ljungdahl pathway of carbon fixation as described, i.e., by Ragsdale, *Biochim Biophys Acta*, 1784: 1873-1898, 2008. "Wood-Ljungdahl microorganisms" refers, predictably, to microorganisms containing the Wood-Ljungdahl pathway. Generally, the microorganism of the invention contains a native Wood-Ljungdahl pathway. Herein, a Wood-Ljungdahl pathway may be a native, unmodified Wood-Ljungdahl pathway or it may be a Wood-Ljungdahl pathway with some degree of genetic modification (i.e., overexpression, heterologous expression, knockout, etc.) so long as it still functions to convert CO, $CO_2$, and/or $H_2$ to acetyl-CoA.

"C1" refers to a one-carbon molecule, for example, CO, $CO_2$, $CH_4$, or $CH_3OH$. "C1-oxygenate" refers to a one-carbon molecule that also comprises at least one oxygen atom, for example, CO, $CO_2$, or $CH_3OH$. "C1-carbon source" refers a one carbon-molecule that serves as a partial or sole carbon source for the microorganism of the invention. For example, a C1-carbon source may comprise one or more of CO, $CO_2$, $CH_4$, $CH_3OH$, or $CH_2O_2$. Preferably, the C1-carbon source comprises one or both of CO and $CO_2$. A "C1-fixing microorganism" is a microorganism that has the ability to produce one or more products from a C1-carbon source. Typically, the microorganism of the invention is a C1-fixing bacterium.

An "anaerobe" is a microorganism that does not require oxygen for growth. An anaerobe may react negatively or even die if oxygen is present above a certain threshold. However, some anaerobes are capable of tolerating low levels of oxygen (i.e., 0.000001-5 vol % oxygen). Typically, the microorganism of the invention is an anaerobe.

"Acetogens" are obligately anaerobic bacteria that use the Wood-Ljungdahl pathway as their main mechanism for energy conservation and for synthesis of acetyl-CoA and acetyl-CoA-derived products, such as acetate (Ragsdale, *Biochim Biophys Acta*, 1784: 1873-1898, 2008). In particular, acetogens use the Wood-Ljungdahl pathway as a (1) mechanism for the reductive synthesis of acetyl-CoA from $CO_2$, (2) terminal electron-accepting, energy conserving process, (3) mechanism for the fixation (assimilation) of $CO_2$ in the synthesis of cell carbon (Drake, Acetogenic Prokaryotes, In: The Prokaryotes, $3^{rd}$ edition, p. 354, New York, N.Y., 2006). All naturally occurring acetogens are C1-fixing, anaerobic, autotrophic, and non-methanotrophic. Typically, the microorganism of the invention is an acetogen.

An "ethanologen" is a microorganism that produces or is capable of producing ethanol. Typically, the microorganism of the invention is an ethanologen.

An "autotroph" is a microorganism capable of growing in the absence of organic carbon. Instead, autotrophs use inorganic carbon sources, such as CO and/or $CO_2$. Typically, the microorganism of the invention is an autotroph.

A "carboxydotroph" is a microorganism capable of utilizing CO as a sole source of carbon and energy. Typically, the microorganism of the invention is a carboxydotroph.

A "methanotroph" is a microorganism capable of utilizing methane as a sole source of carbon and energy. In certain embodiments, the microorganism of the invention is a methanotroph or is derived from a methanotroph. In other embodiments, the microorganism of the invention is not a methanotroph or is not derived from a methanotroph.

"Substrate" refers to a carbon and/or energy source for the microorganism of the invention. Typically, the substrate is gaseous and comprises a C1-carbon source, for example, CO, $CO_2$, and/or $CH_4$. Preferably, the substrate comprises a C1-carbon source of CO or CO+$CO_2$. The substrate may further comprise other non-carbon components, such as $H_2$, $N_2$, or electrons.

The term "co-substrate" refers to a substance that, while not necessarily being the primary energy and material source for product synthesis, can be utilised for product synthesis when added to another substrate, such as the primary substrate.

The substrate and/or C1-carbon source may be a waste gas obtained as a by-product of an industrial process or from some other source, such as from automobile exhaust fumes or biomass gasification. In certain embodiments, the industrial process is selected from the group consisting gas from carbohydrate fermentation, gas from cement making, pulp and paper making, steel making, oil refining and associated petrochemical production, coke production, anaerobic or aerobic digestion, synthesis gas (derived from sources including but not limited to biomass, liquid waste streams, solid waste streams, municipal streams, fossil resources including natural gas, coal and oil), natural gas extraction, oil extraction, metallurgical processes, for production and/or refinement of aluminium, copper, and/or ferroalloys, geological reservoirs, and catalytic processes (derived from steam sources including but not limited to steam methane reforming, steam naphtha reforming, petroleum coke gasification, catalyst regeneration—fluid catalyst cracking, catalyst regeneration-naphtha reforming, and dry methane reforming). In various instances, the substrate and/or C1-carbon source may be captured from the industrial process before it is emitted into the atmosphere, using any convenient method.

The composition of the substrate may have a significant impact on the efficiency and/or cost of the reaction. For example, the presence of oxygen ($O_2$) may reduce the efficiency of an anaerobic fermentation process. Depending on the composition of the substrate, it may be desirable to treat, scrub, or filter the substrate to remove any undesired impurities, such as toxins, undesired components, or dust particles, and/or increase the concentration of desirable components.

In certain embodiments, the fermentation is performed in the absence of carbohydrate substrates, such as sugar, starch, lignin, cellulose, or hemicellulose.

The microorganism of the invention may be cultured with the gas stream to produce one or more products. For instance, the microorganism of the invention may produce or may be engineered to produce ethanol (WO 2007/117157), acetate (WO 2007/117157), butanol (WO 2008/115080 and WO 2012/053905), butyrate (WO 2008/115080), 2,3-butanediol (WO 2009/151342 and WO 2016/094334), lactate (WO 2011/112103), butene (WO 2012/024522), butadiene (WO 2012/024522), methyl ethyl ketone (2-butanone) (WO 2012/024522 and WO 2013/185123), ethylene (WO 2012/026833), acetone (WO 2012/115527), isopropanol (WO 2012/115527), lipids (WO 2013/036147), 3-hydroxypropionate (3-HP) (WO 2013/180581), terpenes, including isoprene (WO 2013/180584), fatty acids (WO 2013/191567), 2-butanol (WO 2013/185123), 1,2-propanediol (WO 2014/036152), 1-propanol (WO 2014/0369152), chorismate-derived products (WO 2016/191625), 3-hydroxybutyrate (WO 2017/066498), and 1,3-butanediol (WO 2017/0066498). In addition to one or more target products, the microorganism of the invention may also produce ethanol, acetate, and/or 2,3-butanediol. In certain embodiments, microbial biomass itself may be considered a product. These products may be further converted to produce at least one component of diesel, jet fuel, and/or gasoline. Additionally, the microbial biomass may be further processed to produce a single cell protein (SCP).

A "single cell protein" (SCP) refers to a microbial biomass that may be used in protein-rich human and/or animal feeds, often replacing conventional sources of protein supplementation such as soymeal or fishmeal. To produce a single cell protein, or other product, the process may comprise additional separation, processing, or treatments steps. For example, the method may comprise sterilizing the microbial biomass, centrifuging the microbial biomass, and/or drying the microbial biomass. In certain embodiments, the microbial biomass is dried using spray drying or paddle drying. The method may also comprise reducing the nucleic acid content of the microbial biomass using any method known in the art, since intake of a diet high in nucleic acid content may result in the accumulation of nucleic acid degradation products and/or gastrointestinal distress. The single cell protein may be suitable for feeding to animals, such as livestock or pets. In particular, the animal feed may be suitable for feeding to one or more beef cattle, dairy cattle, pigs, sheep, goats, horses, mules, donkeys, deer, buffalo/bison, llamas, alpacas, reindeer, camels, bantengs, gayals, yaks, chickens, turkeys, ducks, geese, quail, guinea fowl, squabs/pigeons, fish, shrimp, crustaceans, cats, dogs, and rodents. The composition of the animal feed may be tailored to the nutritional requirements of different animals. Furthermore, the process may comprise blending or combining the microbial biomass with one or more excipients.

An "excipient" may refer to any substance that may be added to the microbial biomass to enhance or alter the form, properties, or nutritional content of the animal feed. For example, the excipient may comprise one or more of a carbohydrate, fiber, fat, protein, vitamin, mineral, water, flavour, sweetener, antioxidant, enzyme, preservative, probiotic, or antibiotic. In some embodiments, the excipient may be hay, straw, silage, grains, oils or fats, or other plant material. The excipient may be any feed ingredient identified in Chiba, Section 18: Diet Formulation and Common Feed Ingredients, Animal Nutrition Handbook, $3^{rd}$ revision, pages 575-633, 2014.

A "native product" is a product produced by a genetically unmodified microorganism. For example, ethanol, acetate, and 2,3-butanediol are native products of *Clostridium autoethanogenum*, *Clostridium ljungdahlii*, and *Clostridium ragsdalei*. A "non-native product" is a product that is produced by a genetically modified microorganism, but is not produced by a genetically unmodified microorganism from which the genetically modified microorganism is derived.

"Selectivity" refers to the ratio of the production of a target product to the production of all fermentation products produced by a microorganism. The microorganism of the invention may be engineered to produce products at a certain selectivity or at a minimum selectivity. In one embodiment, a target product account for at least about 5 wt. %, 10 wt. %, 15 wt. %, 20 wt. %, 30 wt. %, 50 wt. %, 75 wt. %, or 90 wt. % of all fermentation products produced by the microorganism of the invention. In one embodiment, the target product accounts for at least 10 wt. % of all fermentation products produced by the microorganism of the invention, such that the microorganism of the invention has a selectivity for the target product of at least 10 wt. %. In another embodiment, the target product accounts for at least 30 wt. % of all fermentation products produced by the microorganism of the invention, such that the microorganism of the invention has a selectivity for the target product of at least 30 wt. %. In one embodiment, the target product accounts for at least 90 wt. % of all fermentation products produced by the microorganisms, such that the microorganism of the invention has a selectivity for the target product of at least 90 wt. %.

Typically, the culture is performed in a bioreactor. The term "bioreactor" includes a culture/fermentation device consisting of one or more vessels, towers, or piping arrangements, such as a continuous stirred tank reactor (CSTR), immobilized cell reactor (ICR), trickle bed reactor (TBR), bubble column, gas lift fermenter, static mixer, or other vessel or other device suitable for gas-liquid contact. In some embodiments, the bioreactor may comprise a first growth reactor and a second culture/fermentation reactor. The substrate may be provided to one or both of these reactors. As used herein, the terms "culture" and "fermentation" are used interchangeably. These terms encompass both the growth phase and product biosynthesis phase of the culture/fermentation process.

The culture is generally maintained in an aqueous culture medium that contains nutrients, vitamins, and/or minerals sufficient to permit growth of the microorganism. Preferably the aqueous culture medium is an anaerobic microbial growth medium, such as a minimal anaerobic microbial growth medium. Suitable media are well known in the art.

The culture/fermentation should desirably be carried out under appropriate conditions for production of the target product. Typically, the culture/fermentation is performed under anaerobic conditions. Reaction conditions to consider include pressure (or partial pressure), temperature, gas flow rate, liquid flow rate, media pH, media redox potential, agitation rate (if using a continuous stirred tank reactor), inoculum level, maximum gas substrate concentrations to ensure that gas in the liquid phase does not become limiting, and maximum product concentrations to avoid product inhibition. In particular, the rate of introduction of the substrate may be controlled to ensure that the concentration of gas in the liquid phase does not become limiting, since products may be consumed by the culture under gas-limited conditions.

Operating a bioreactor at elevated pressures allows for an increased rate of gas mass transfer from the gas phase to the liquid phase. Accordingly, it is generally preferable to perform the culture/fermentation at pressures higher than atmospheric pressure. Also, since a given gas conversion rate is, in part, a function of the substrate retention time and retention time dictates the required volume of a bioreactor, the use of pressurized systems can greatly reduce the volume of the bioreactor required and, consequently, the capital cost of the culture/fermentation equipment. This, in turn, means that the retention time, defined as the liquid volume in the bioreactor divided by the input gas flow rate, can be reduced when bioreactors are maintained at elevated pressure rather than atmospheric pressure. The optimum reaction conditions will depend partly on the particular microorganism used. However, in general, it is preferable to operate the fermentation at a pressure higher than atmospheric pressure. Also, since a given gas conversion rate is in part a function of substrate retention time and achieving a desired retention time in turn dictates the required volume of a bioreactor, the use of pressurized systems can greatly reduce the volume of the bioreactor required, and consequently the capital cost of the fermentation equipment.

Target products may be separated or purified from a fermentation broth using any method or combination of methods known in the art, including, for example, fractional distillation, evaporation, pervaporation, gas stripping, phase separation, and extractive fermentation, including for example, liquid-liquid extraction. In certain embodiments, target products are recovered from the fermentation broth by continuously removing a portion of the broth from the bioreactor, separating microbial cells from the broth (conveniently by filtration), and recovering one or more target products from the broth. Alcohols and/or acetone may be recovered, for example, by distillation. Acids may be recovered, for example, by adsorption on activated charcoal. Separated microbial cells are preferably returned to the bioreactor. The cell-free permeate remaining after target products have been removed is also preferably returned to the bioreactor. Additional nutrients (such as B vitamins) may be added to the cell-free permeate to replenish the medium before it is returned to the bioreactor.

DESCRIPTION

Carbon monoxide and oxygen can be produced by an electrolyzer process, defined by the following molar stoichiometric reaction: $2CO_2$+electricity→$2CO+O_2$. The carbon monoxide produced by electrolysis can be used as a feedstock for gas fermentation. Additionally, it is considered that the produced CO can be used alongside feedstock from an industrial process, as a means to provide additional feedstock and/or improve the fermentation substrate composition.

The electrolyzer process is also capable of producing hydrogen from water, defined by the following molar stoichiometric reaction: $2H_2O+\text{electricity} \rightarrow 2H_2+O_2$. The hydrogen produced by electrolysis can be used as a feedstock for gas fermentation. This hydrogen may be used alongside feedstock from an industrial process, as a means to provide additional feedstock and/or improve the fermentation substrate composition.

The use of the electrolyzer feedstock may be used at times when economically viable. In certain instances, the feedstock from the electrolyzer process may increase the efficiency of the fermentation process by reducing the costs associated with production.

The $CO_2$-containing substrate utilized by the electrolyzer process for producing carbon monoxide may be derived from a number of sources. The $CO_2$-containing gaseous substrate may be derived, at least in part, from any gas containing $CO_2$, selected from the group comprising: gas from carbohydrate fermentation, gas from cement making, pulp and paper making, steel making, oil refining and associated processes, petrochemical production, coke production, anaerobic or aerobic digestion, synthesis gas (derived from sources including but not limited to biomass, liquid waste streams, solid waste streams, municipal streams, fossil resources including natural gas, coal and oil), natural gas extraction, oil extraction, metallurgical processes, for production and/or refinement of aluminium, copper, and/or ferroalloys, geological reservoirs, and catalytic processes (derived from steam sources including but not limited to steam methane reforming, steam naphtha reforming, petroleum coke gasification, catalyst regeneration—fluid catalyst cracking, catalyst regeneration-naphtha reforming, and dry methane reforming). Additionally, the substrate may be captured from the industrial process before it is emitted into the atmosphere, using any conventional method. Furthermore, the $CO_2$-containing substrate may be derived from a combination of two or more of the above mentioned sources.

Gas streams typically will not be a pure $CO_2$ stream, and will contain proportions of at least one other component. For instance, each source may have differing proportions of $CO_2$, CO, $H_2$, and various constituents. Due to the varying proportions, the gas stream may be processed prior to being introduced to the bioreactor and/or the electrolysis module. The processing of the gas stream includes the removal and/or conversion of various constituents that may be microbe inhibitors and/or catalyst inhibitors. Preferably, the catalyst inhibitors are removed and/or converted prior to being passed to the electrolysis module, and the microbe inhibitors are removed and/or converted prior to being passed to the bioreactor.

Typical constituents found in the gas stream that may need to be removed and/or converted include, but are not limited to, sulphur compounds, aromatic compounds, alkynes, alkenes, alkanes, olefins, nitrogen compounds, phosphorous-containing compounds, particulate matter, solids, oxygen, oxygenates, halogenated compounds, silicon containing compounds, carbonyls, metals, alcohols, esters, ketones, peroxides, aldehydes, ethers, and tars.

These constituents may be removed by conventional removal modules known in the art. These removal modules may be selected from the following: hydrolysis module, acid gas removal module, deoxygenation module, catalytic hydrogenation module, particulate removal module, chloride removal module, tar removal module, and hydrogen cyanide removal module.

FIG. 1 shows the integration of an industrial process 110 and an electrolyzer process 120 with a fermentation process 130. The fermentation process 130 is capable of receiving C1 feedstock from the industrial process 110 and electrolyzer feedstock from the electrolyzer process 120. The electrolyzer feedstock from the electrolyzer process 120 may be fed to the fermentation process 130 intermittently. Preferably, the C1 feedstock from the industrial process 110 is fed via a conduit 112 to the fermentation process 130, and the electrolyzer feedstock from the electrolyzer process 120 is fed via a conduit 122 to the fermentation process 130. The fermentation process 130 utilizes the electrolyzer feedstock from the electrolyzer process 110 and the C1 feedstock from the industrial process 110 to produce one or more fermentation product 136.

In certain instances, the electrolyzer feedstock comprises CO. In certain instances, the electrolyzer feedstock comprises $H_2$. In certain instances, the electrolyzer feedstock from the electrolyzer process 120 displaces at least a portion of the C1 feedstock from the industrial process 110. Preferably, the electrolyzer feedstock displaces at least a portion of the C1 feedstock as a function of the cost per unit of the C1 feedstock and the cost per unit of the electrolyzer feedstock. In various instances, the electrolyzer feedstock displaces at least a portion of the C1 feedstock when the cost per unit of electrolyzer feedstock is less than the cost per unit of C1 feedstock.

The cost per unit of electrolyzer feedstock may be less than the cost per unit of the C1 feedstock when the cost of electricity is reduced. In certain instances, the cost of electricity is reduced due to the electricity being sourced from a renewable energy source. In certain instances, the renewable energy source is selected from the group consisting of solar, hydro, wind, geothermal, biomass, and nuclear.

The electrolyzer feedstock from the electrolyzer process 120 may supplement the C1 feedstock from the industrial process 110. Preferably, the electrolyzer feedstock supplements the C1 feedstock when the supply of the C1 feedstock is insufficient for the fermentation process. In certain instances, the electrolyzer feedstock supplements the C1 feedstock as a function of the cost per unit of the electrolyzer feedstock and the value per unit of the fermentation product 136. In certain instances, the electrolyzer feedstock supplements the C1 feedstock as a function of the cost per unit of the C1 feedstock, the cost per unit of the electrolyzer feedstock, and the value per unit of the fermentation product 136. Preferably, the electrolyzer feedstock from the electrolyzer process 120 supplements the C1 feedstock when the cost per unit of the electrolyzer feedstock is less than the value per unit of the fermentation product 136. In various instances, the supplementing of the C1 feedstock comprising $CO_2$ with electrolyzer feedstock comprising $H_2$ increases the amount of $CO_2$ fixed in the one or more fermentation product 136.

Figure 2:
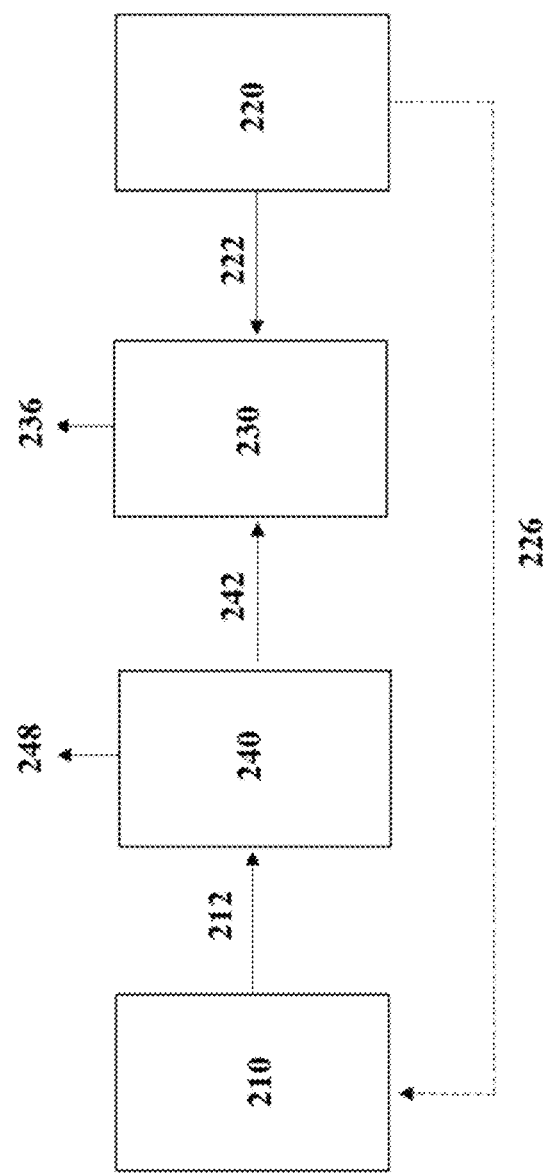
FIG. 2 is a schematic flow diagram depicting the integration of an industrial process and an electrolyzer process with a fermentation process further including a removal module for processing the C1 feedstock, in accordance with one aspect of the invention.

In particular instances, the C1 feedstock contains one or more constituent, and may require treatment prior to being sent to the fermentation process. FIG. 2 shows a removal module 240 for treating the C1 feedstock from the industrial process 210. When using a removal module 240, the C1 feedstock from the industrial process 210 is sent from the industrial process 210 to the removal module 240 via a conduit 212. Preferably, the removal module 240 removes and/or converts one or more constituent 248 in the C1 feedstock. The treated C1 feedstock is sent from the removal module 240 to the fermentation process 230 via a conduit 242.

In certain instances, the C1 feedstock is treated prior to being sent to the fermentation process, where the electrolyzer feedstock from the electrolyzer process 220 is not treated prior to being sent to the fermentation process 230. When not being treated, the electrolyzer feedstock may be sent via a conduit 222 from the electrolyzer process 220 to the fermentation process 230. Preferably, the C1 feedstock from the industrial process 210 and the electrolyzer feedstock from the electrolyzer process 220 are used in the fermentation process 230 to produce one or more fermentation product 236.

Figure 3:
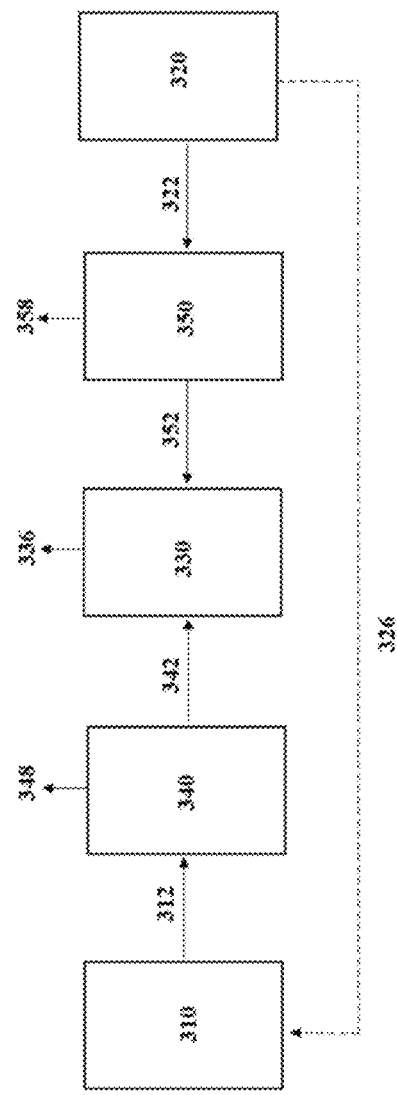
FIG. 3 is a schematic flow diagram depicting the integration of an industrial process and an electrolyzer process with a fermentation process further including a removal module for processing the electrolyzer feedstock, in accordance with one aspect of the invention.

In particular instances, the electrolyzer feedstock contains one or more constituent, and may require treatment prior to being sent to the fermentation process. FIG. 3 shows a removal module 350 for treating the electrolyzer feedstock from the electrolyzer process 320. When using a removal module 350, the electrolyzer feedstock from the electrolyzer process 320 is sent from the electrolyzer process 320 to the removal module 350 via a conduit 322. Preferably, the removal module 350 removes and/or converts one or more constituent 358 in the electrolyzer feedstock. In certain instances, constituent removed by the removal module 350 is oxygen, which is produced as a by-product of the electrolysis process. The treated electrolyzer feedstock is sent from the removal module 350 to the fermentation process 330 via a conduit 352.

In certain instances, both the C1 feedstock and the electrolyzer feedstock are treated prior to being sent to the fermentation process. When treating the C1 feedstock, the C1 feedstock is sent from the industrial process 310 to the removal module 340 via a conduit 312 to remove and/or convert one or more constituent 348 in the C1 feedstock. The treated C1 feedstock is sent from the removal module 340 to the fermentation process 330 via a conduit 342. Preferably, the C1 feedstock from the industrial process 310 and the electrolyzer feedstock from the electrolyzer process 320 are used in the fermentation process 330 to produce one or more fermentation product 336.

Figure 4:
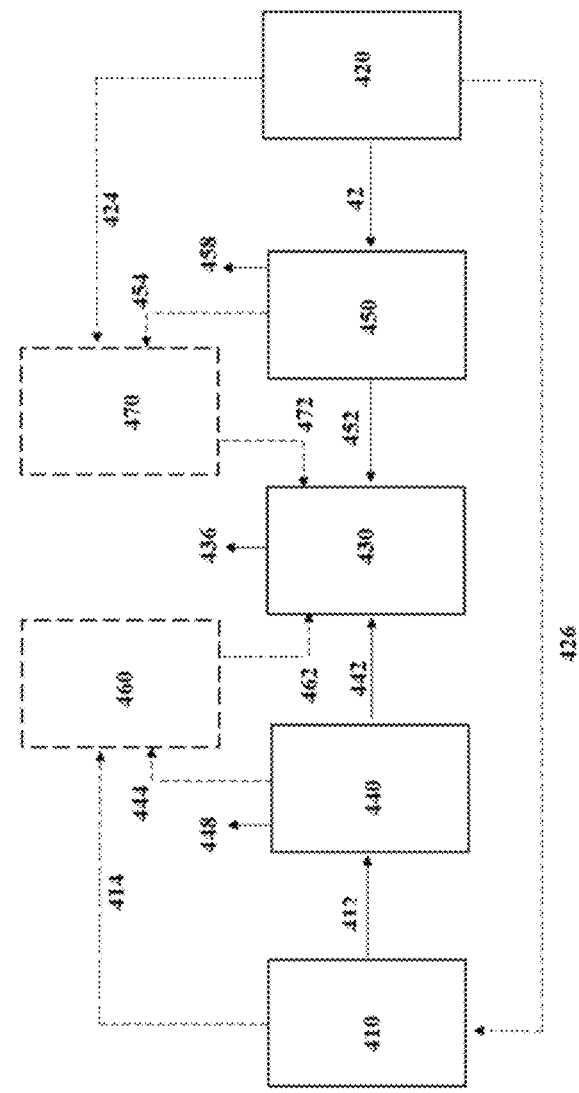
FIG. 4 is a schematic flow diagram depicting the integration of an optional pressure module for pressurizing the electrolyzer feedstock, and an optional pressure module for pressuring the C1 feedstock, in accordance with one aspect of the invention.

The feedstock may be pressurized prior to being passed to the fermentation process. FIG. 4 shows a pressure module 460 for pressurizing the C1 feedstock and a pressure module 470 for pressurizing the electrolyzer feedstock. In certain instances, the C1 feedstock may be pressurized, while the electrolyzer feedstock is not pressurized. In certain instances, the electrolyzer feedstock may be pressurized, while the C1 feedstock is not pressurized. In various instances, the feedstock is pressurized without treatment. In various instances, the feedstock is pressurized following treatment. When pressurizing the C1 feedstock following treatment, the C1 feedstock is sent from the industrial process 410 to the removal module 440 via a conduit 412 to remove and/or convert one or more constituent 448. The treated C1 feedstock is sent from the removal module 440 to the pressure module 460 via a conduit 444. The pressurized C1 feedstock is sent from the pressure module 460 to the fermentation process 430 via a conduit 462. In instances where the C1 feedstock is not pressurized, the C1 feedstock may be sent from the removal module 440 to the fermentation process 430 via a conduit 442. In various instances where the C1 feedstock is pressurized without treatment, the C1 feedstock is sent from the industrial process 410 to the pressure module 460 via a conduit 414. When pressurizing the electrolyzer feedstock following treatment, the electrolyzer feedstock is sent from the electrolyzer process 420 to the removal module 450 via a conduit 422 to remove and/or convert one or more constituent 458. The treated electrolyzer feedstock is sent from the removal module 450 to the pressure module 470 via a conduit 454. The pressurized electrolyzer feedstock is sent from the pressure module 470 to the fermentation process 430 via a conduit 472. In instances where the electrolyzer feedstock is not pressurized, the electrolyzer feedstock may be sent from the removal module 450 to the fermentation process 430 via a conduit 452. In various instances where the electrolyzer feedstock is pressurized without treatment, the electrolyzer feedstock is sent from the electrolyzer process 420 to the pressure module 470 via a conduit 424. Preferably, the C1 feedstock from the industrial process 410 and the electrolyzer feedstock from the electrolyzer process 420 are used in the fermentation process 430 to produce one or more fermentation product 436.

Figure 5:
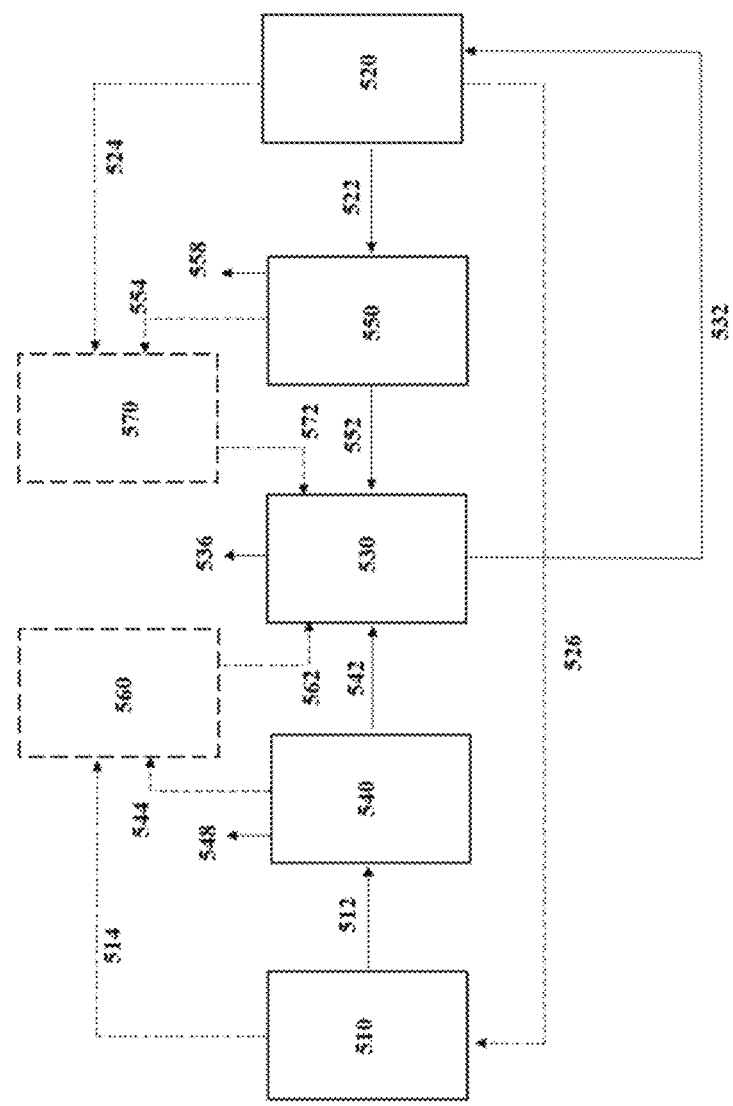
FIG. 5 is a schematic flow diagram depicting the integration of an electrolyzer process and a fermentation process where a post-fermentation gaseous substrate is passed from the fermentation process to the electrolyzer process, in accordance with one aspect of the invention.

The fermentation process may produce a post-fermentation gaseous substrate in addition to the one or more fermentation product. This post-fermentation gaseous substrate may contain relatively high proportions of $CO_2$. In various instances, the post-fermentation gaseous substrate may be sent to the electrolyzer process. FIG. 5 shows the passing of a post-fermentation gaseous substrate from the fermentation process 530 to the electrolysis process 520 via a conduit 532. Preferably, the fermentation process 530 produces one or more fermentation product 536 and a post-fermentation gaseous substrate by utilizing feedstock from one or both of the industrial process 510 and/or the electrolyzer process 520. The C1 feedstock from the industrial process 510 may be pressurized by way of a pressure module 560. Pressurization may be completed with or without treatment. When pressurizing the C1 feedstock following treatment, the C1 feedstock is sent from the industrial process 510 to the removal module 540 via a conduit 512 to remove and/or convert one or more constituent 548. The treated C1 feedstock is sent from the removal module 540 to the pressure module 560 via a conduit 544. The pressurized C1 feedstock is sent from the pressure module 560 to the fermentation process 530 via a conduit 562. In instances where the C1 feedstock is not pressurized, the C1 feedstock may be sent from the removal module 540 to the fermentation process 530 via a conduit 542. In various instances where the C1 feedstock is pressurized without treatment, the C1 feedstock is sent from the industrial process 510 to the pressure module 560 via a conduit 514. When pressurizing the electrolyzer feedstock following treatment, the electrolyzer feedstock is sent from the electrolyzer process 520 to the removal module 550 via a conduit 522 to remove and/or convert one or more constituent 558. The treated electrolyzer feedstock is sent from the removal module 550 to the pressure module 570 via a conduit 554. The pressurized electrolyzer feedstock is sent from the pressure module 570 to the fermentation process 530 via a conduit 572. In instances where the electrolyzer feedstock is not pressurized, the electrolyzer feedstock may be sent from the removal module 550 to the fermentation process 530 via a conduit 552. In various instances where the electrolyzer feedstock is pressurized without treatment, the electrolyzer feedstock is sent from the electrolyzer process 520 to the pressure module 570 via a conduit 524.

Figure 6:
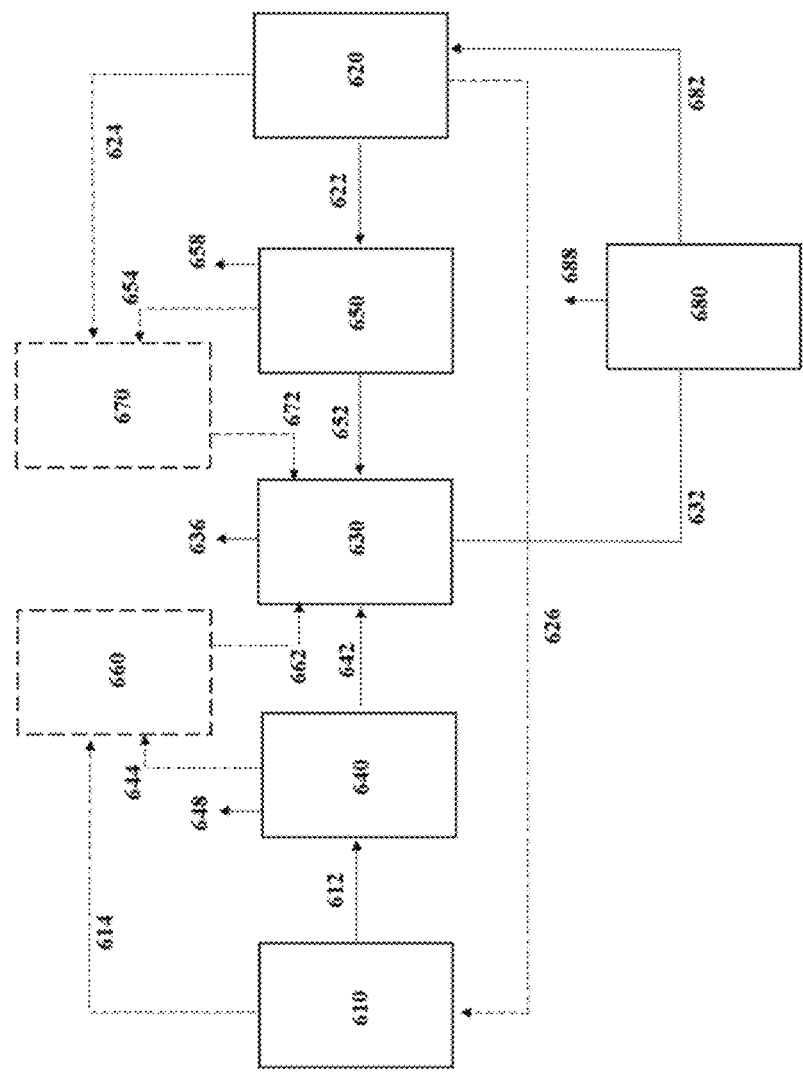
FIG. 6 is a schematic flow diagram depicting integration of a removal module for processing the post-fermentation gaseous substrate, in accordance with one aspect of the invention.

The post-fermentation gaseous substrate may contain one or more constituent that may need to be removed and/or converted prior to being passed to the electrolyzer process. FIG. 6 shows the passing of the post-fermentation gaseous substrate to a removal module 680 via a conduit 632 to remove and/or convert one or more constituent 688. The treated post-fermentation gaseous substrate is then passed from the removal module 680 to the electrolyzer process 620 via a conduit 682.

One or more of the constituents in the post-fermentation gaseous substrate may be produced, introduced, and/or concentrated by the fermentation process. In various embodiments, the one or more constituent produced, introduced, and/or concentrated by the fermentation step comprises sulphur. These constituents, including sulphur, may decrease the efficiency of the electrolyzer process 620 if not removed and/or converted. Preferably, the post-fermentation gaseous substrate is treated so that it is suitable for electrolysis. By utilizing the post-fermentation gaseous substrate in the electrolysis module 620, an increased proportion of carbon may be captured by the process.

Preferably, the fermentation process 630 utilizes the feedstock from one or both of the industrial process 610 an/or the electrolyzer process 620 to produce one or more fermentation product 636, where at least a portion of the electrolyzer feedstock may be derived, at least in part, from the post-fermentation gaseous substrate. The C1 feedstock from the industrial process 610 may be pressurized by way of a pressure module 660. Pressurization may be completed with or without treatment. When pressurizing the C1 feedstock following treatment, the C1 feedstock is sent from the industrial process 610 to the removal module 640 via a conduit 612 to remove and/or convert one or more constituent 648. The treated C1 feedstock is sent from the removal module 640 to the pressure module 660 via a conduit 644. The pressurized C1 feedstock is sent from the pressure module 660 to the fermentation process 630 via a conduit 662. In instances where the C1 feedstock is not pressurized, the C1 feedstock may be sent from the removal module 640 to the fermentation process 630 via a conduit 642. In various instances where the C1 feedstock is pressurized without treatment, the C1 feedstock is sent from the industrial process 610 to the pressure module 660 via a conduit 614. When pressurizing the electrolyzer feedstock following treatment, the electrolyzer feedstock is sent from the electrolyzer process 620 to the removal module 650 via a conduit 622 to remove and/or convert one or more constituent 658. The treated electrolyzer feedstock is sent from the removal module 650 to the pressure module 670 via a conduit 654. The pressurized electrolyzer feedstock is sent from the pressure module 670 to the fermentation process 630 via a conduit 672. In instances where the electrolyzer feedstock is not pressurized, the electrolyzer feedstock may be sent from the removal module 650 to the fermentation process 630 via a conduit 652. In various instances where the electrolyzer feedstock is pressurized without treatment, the electrolyzer feedstock is sent from the electrolyzer process 620 to the pressure module 670 via a conduit 624.

Figure 7:
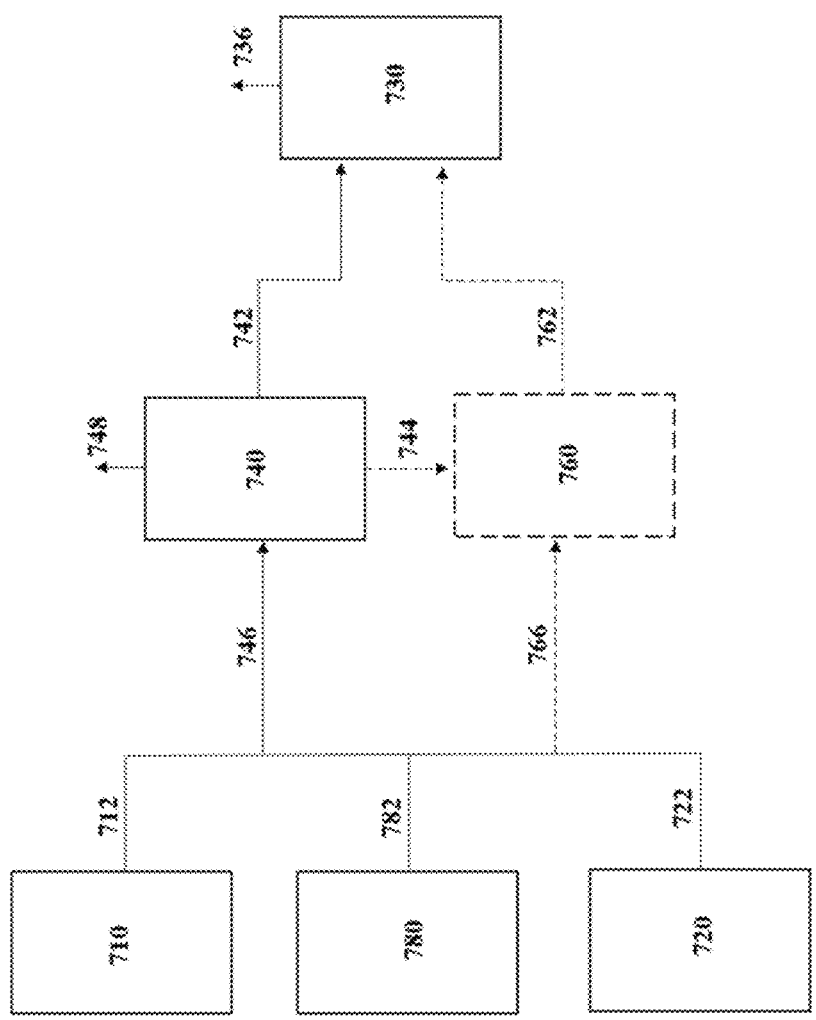
FIG. 7 is a schematic flow diagram depicting the blending of one or more of the streams from one or more electrolyzer process and/or the industrial process, in accordance with one aspect of the invention.

In various embodiments, the feedstock from one or more electrolyzer process and the industrial process may be blended. FIG. 7 shows the blending of feedstock from the industrial process 710 and multiple electrolyzer processes 720, 780. The C1 feedstock from the industrial process 710 is sent via a conduit 712 to be blended. A first electrolyzer feedstock from a first electrolyzer process 720 is sent via a conduit 722 to be blended. A second electrolyzer feedstock from a second electrolyzer process 780 is sent via a conduit 782 to be blended. In certain instances, only the electrolyzer feedstock from the first electrolyzer process 720 and the C1 feedstock from the industrial process 710 are blended. In certain instances, only the electrolyzer feedstock from the second electrolyzer process 780 and the C1 feedstock from the industrial process 710 are blended. In certain instances, only the electrolyzer feedstock from the first electrolyzer process 720 and the electrolyzer feedstock from the second electrolyzer process 780 are blended. The blended feedstock may be sent via a conduit 746 to one or more removal module 740 to remove and/or convert one or more constituent 748.

The blended feedstock may be pressurized by way of a pressure module 760. Pressurization may be completed with or without treatment. When pressurizing the blended feedstock following treatment, the blended feedstock is sent via a conduit 746 to the removal module 740 to remove and/or convert one or more constituent 748. The treated blended feedstock is sent from the removal module 740 to the pressure module 760 via a conduit 744. The pressurized blended feedstock is sent from the pressure module 760 to the fermentation process 730 via a conduit 762 to produce one or more fermentation product 736. In instances where the blended feedstock is not pressurized, the blended feedstock may be sent from the removal module 740 to the fermentation process 730 via a conduit 742. In various instances where the blended feedstock is pressurized without treatment, the blended feedstock is sent via a conduit 766 to the pressure module 760.

In various instances the feedstock from one or more process may be intermittent while the other feedstock from one is more process is continuous. In certain instances, the electrolyzer feedstock from one or more electrolyzer process 720, 780 are intermittent, while the C1 feedstock from the industrial process 710 is continuous. In certain instances, the C1 feedstock from the industrial process 710 is intermittent, while the electrolyzer feedstock from one or more electrolyzer process 720, 780 are continuous. In certain instances, electrolyzer feedstock from the first electrolyzer process 720 is intermittent, while the electrolyzer feedstock from the second electrolyzer process 780 is continuous. In certain instances, the electrolyzer feedstock from the second electrolyzer process 780 is intermittent, while the electrolyzer feedstock from the first electrolyzer process 720 is continuous.

In various embodiments, at least a portion of the electrolyzer feedstock may be sent to storage. Certain industrial processes may include storage means for long-term or short-term storage of gaseous substrates and/or liquid substrates. In instances where at least a portion of the electrolyzer feedstock is sent to storage, the electrolyzer feedstock may be sent to the same storage means utilized by the industrial process, for example an existing gas holder at a steel mill. At least a portion of the electrolyzer feedstock may be sent to independent storage means, where electrolyzer feedstock is stored separately from the C1 feedstock from the industrial process. In certain instances, this stored feedstock from one or both of the industrial process and/or the one or more electrolyzer processes may be used by the fermentation process at a later time.

In various embodiments, the invention provides an integrated process comprising electrolysis wherein the power supplied for the electrolyzer process is derived, at least in part, from a renewable energy source. In certain instances, the renewable energy source is selected from the group consisting of solar, hydro, wind, geothermal, biomass, and nuclear.

Although the substrate is typically gaseous, the substrate may also be provided in alternative forms. For example, the substrate may be dissolved in a liquid saturated with a CO-containing gas using a microbubble dispersion generator. By way of further example, the substrate may be adsorbed onto a solid support.

In addition to increasing the efficiency of the fermentation process, the electrolyzer process may increase the efficiency of the industrial process. The increase in efficiency of the industrial process may be achieved through use of an electrolyzer by-product, namely, oxygen. Specifically, the $O_2$ by-product of the electrolyzer process may be used by the C1-generating industrial process. Many C1-generating industrial processes are forced to produce $O_2$ to use in their processes. However, by utilizing the $O_2$ by-product from the electrolyzer process, the costs of producing $O_2$ can be reduced and/or eliminated. The passing of the $O_2$ by-product from the electrolyzer process is exemplified in FIGS. 1-6 where the $O_2$ by-product is passed through a conduit, 126, 226, 326, 426, 526, and 626, respectively, from the electrolyzer process to the industrial process.

Several C1-generating industrial processes involving partial oxidation reactions, require an $O_2$ input. Exemplary industrial processes include Basic Oxygen Furnace (BOF) reactions; COREX or FINEX steel making processes, Blast Furnace (BF) processes, ferroalloy production processes, titanium dioxide production processes, and gasification processes. Gasification processes include, but are not limited to, municipal solid waste gasification, biomass gasification, pet coke gasification and coal gasification. In one or more of these industrial processes, the $O_2$ from the carbon dioxide electrolyzer process may be used to off-set or completely replace the $O_2$ typically supplied through air separation.

Figure 8:
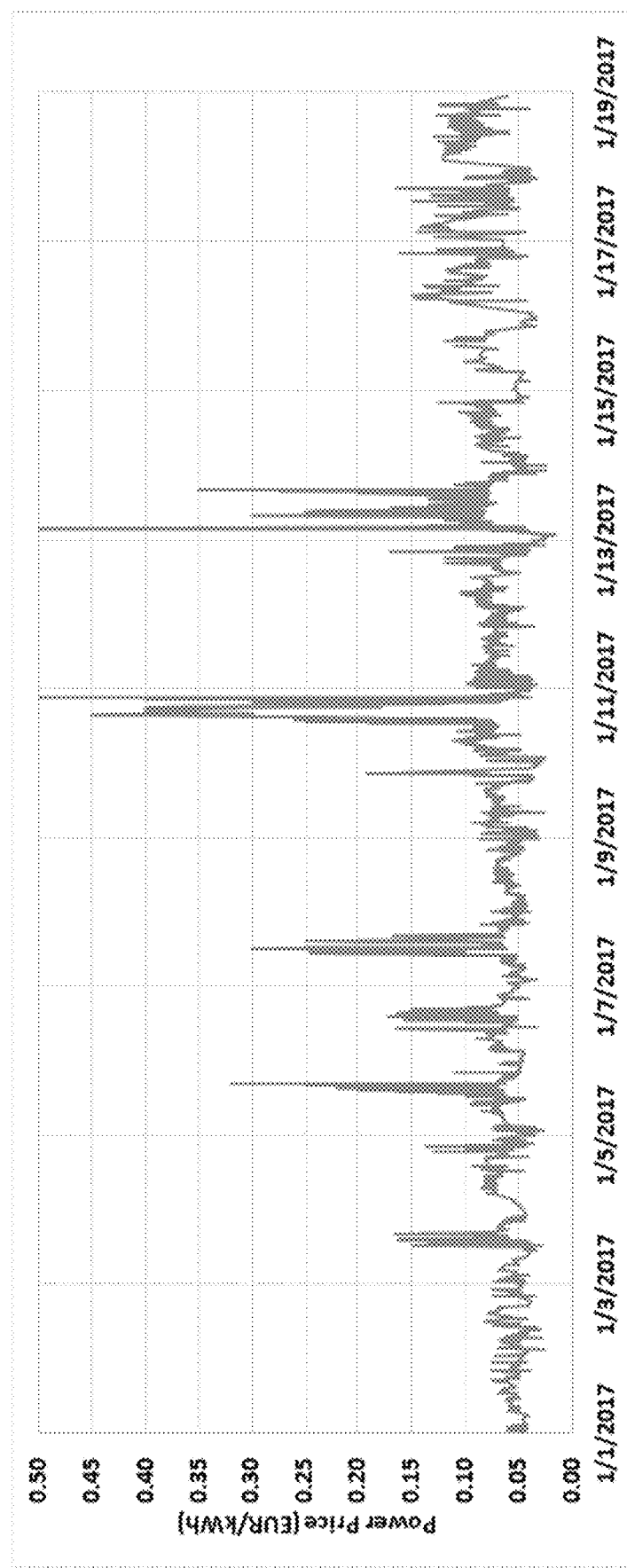
FIG. 8 is a graph showing the price of electricity in Belgium over a period of nineteen days, with an average of one data point every four minutes.

The need for the current invention is illustrated by FIG. 8, which depicts the price of electricity in Belgium over a nineteen-day period. FIG. 8 highlights the difference between the average price of electricity (roughly 0.05 EUR/kWh) and the minimum/maximum price of electricity over a period of time. Due to the vast difference in the price of electricity in a given location, and the effect of electricity price on the efficiency of electrolysis as a gas source for fermentation, it is largely advantageous to have a flexible approach for the utilization of electrolysis. For example, utilizing electrolysis as a gas source for fermentation when electricity is relatively cheap, and discontinuing use for periods of time in which prices are high. This demand-responsive utilization of electrolysis can add tremendous value to a gas fermentation facility.

All references, including publications, patent applications, and patents, cited herein are hereby incorporated by reference to the same extent as if each reference were individually and specifically indicated to be incorporated by reference and were set forth in its entirety herein. The reference to any prior art in this specification is not, and should not be taken as, an acknowledgement that that prior art forms part of the common general knowledge in the field of endeavour in any country.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. The term "consisting essentially of" limits the scope of a composition, process, or method to the specified materials or steps, or to those that do not materially affect the basic and novel characteristics of the composition, process, or method. The use of the alternative (i.e., "or") should be understood to mean either one, both, or any combination thereof of the alternatives. As used herein, the term "about" means ±20% of the indicated range, value, or structure, unless otherwise indicated.

Recitation of ranges of values herein are merely intended to serve as a shorthand method of referring individually to each separate value falling within the range, unless otherwise indicated herein, and each separate value is incorporated into the specification as if it were individually recited herein. For example, any concentration range, percentage range, ratio range, integer range, size range, or thickness range is to be understood to include the value of any integer within the recited range and, when appropriate, fractions thereof (such as one tenth and one hundredth of an integer), unless otherwise indicated.

All methods described herein can be performed in any suitable order unless otherwise indicated herein or otherwise clearly contradicted by context. The use of any and all examples, or exemplary language (i.e., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of operating a fermentation process with a bioreactor containing a bacterial culture in a liquid nutrient medium, the method comprising:
   a. passing a C1 feedstock comprising one or both of CO and $CO_2$ from an industrial process to the bioreactor, wherein the C1 feedstock has a cost per unit;
   b. passing a gaseous $CO_2$-containing substrate and/or a water stream to an electrolyzer process to produce an electrolyzer feedstock comprising CO and/or $H_2$;
   c. determining if the cost per unit of the electrolyzer feedstock is less than or greater than the cost per unit of the C1 feedstock and if the cost per unit of the electrolyzer feedstock is less than the C1 feedstock cost per unit, passing at least a portion of the electrolyzer feedstock from the electrolyzer process to the bioreactor, to displace at least a portion of the C1 feedstock wherein the electrolyzer feedstock has a cost per unit with respect to $H_2$ given by an equation $$\left(\frac{\$z}{MWh}\right) \times \left(\frac{1 MWh}{3.6 GJ_{electricity}}\right) \times \left(x \frac{GJ_{electricity}}{GJ_{H2}}\right) \times \left(y \frac{GJ_{H2}}{GJ_{ethanol}}\right)$$

where z represents the cost of power, x represents the electrolysis efficiency, and y represents the yield of ethanol and with respect to CO by an equation $$\left(\frac{\$z}{MWh}\right) \times \left(\frac{1MWh}{3.6GJ_{electricity}}\right) \times \left(x\frac{GJ_{electricity}}{GJ_{CO}}\right) \times \left(y\frac{GJ_{CO}}{GJ_{ethanol}}\right)$$

where z represents the cost of power, x represents the electrolysis efficiency, and y represents the yield of ethanol; and d. fermenting the culture to produce at least one fermentation product comprising ethanol, wherein the ethanol has a value per unit.

2. The method of claim 1, wherein the C1 feedstock further comprises $H_2$.

3. The method of claim 1, wherein the C1 feedstock is treated to remove one or more constituents prior to passing the C1 feedstock to the bioreactor.

4. The method of claim 3, wherein at least one or more of the constituents removed from the C1 feedstock is selected from the group comprising: sulphur compounds, aromatic compounds, alkynes, alkenes, alkanes, olefins, nitrogen compounds, phosphorous-containing compounds, particulate matter, solids, oxygen, oxygenates, halogenated compounds, silicon containing compounds, carbonyls, metals, alcohols, esters, ketones, peroxides, aldehydes, ethers, and tars.

5. The method of claim 1, wherein the electrolyzer feedstock is treated to remove at least one constituent prior to passing the electrolyzer feedstock to the bioreactor.

6. The method of claim 5, wherein the at least one constituent removed from the electrolyzer feedstock comprises oxygen.

7. The method of claim 1, wherein the C1 feedstock is pressurized prior to passing the C1 feedstock to the bioreactor.

8. The method of claim 1, wherein the electrolyzer feedstock is pressurized prior to passing the electrolyzer feedstock to the bioreactor.

9. The method of claim 1, wherein the fermentation product further comprises at least one product selected from the group consisting of acetate, butyrate, 2,3-butanediol, lactate, butene, butadiene, ketones, methyl ethyl ketone, ethylene, acetone, isopropanol, lipids, 3-hydroypropionate, isoprene, fatty acids, 2-butanol, 1,2-propanediol, and 1-propanol.

10. The method of claim 1, wherein the fermentation product further comprises microbial biomass.

11. The method of claim 1, wherein the electrolyzer process is powered, at least in part, by a renewable energy source.

12. The method of claim 11, wherein the renewable energy source is selected from the group consisting of solar, hydro, wind, geothermal, and biomass.

13. The method of claim 1, wherein the culture further produces a post-fermentation gaseous substrate.

14. The method of claim 13, further comprising passing the post-fermentation gaseous substrate to the electrolyzer process.

15. The method of claim 14, wherein the post-fermentation gaseous substrate is treated to remove one or more constituents prior to being passed to the electrolyzer process.

16. The method of claim 15, wherein the one or more constituents removed from the post-fermentation gaseous substrate is selected from the group comprising: sulphur compounds, aromatic compounds, alkynes, alkenes, alkanes, olefins, nitrogen compounds, phosphorous-containing compounds, particulate matter, solids, oxygen, oxygenates, halogenated compounds, silicon containing compounds, carbonyls, metals, alcohols, esters, ketones, peroxides, aldehydes, ethers, and tars.

17. The method of claim 16, wherein the one or more constituents removed from the post-fermentation gaseous substrate are sulphur compounds.

\* \* \* \* \*